United States Patent
Geiger et al.

(10) Patent No.: US 8,755,635 B2
(45) Date of Patent: Jun. 17, 2014

(54) METHOD AND SYSTEM FOR DATA DEPENDENT MULTI PHASE VISUALIZATION

(75) Inventors: Bernhard Geiger, Cranbury, NJ (US); Ernst Klotz, Uttenreuth (DE); Christophe Chefd'hotel, Jersey City, NJ (US)

(73) Assignee: Siemens Aktiengesellschaft, Munich (DE)

( * ) Notice: Subject to any disclaimer, the term of this patent is extended or adjusted under 35 U.S.C. 154(b) by 591 days.

(21) Appl. No.: 12/512,080

(22) Filed: Jul. 30, 2009

(65) Prior Publication Data

US 2010/0061606 A1 Mar. 11, 2010

Related U.S. Application Data

(60) Provisional application No. 61/087,766, filed on Aug. 11, 2008.

(51) Int. Cl.
*G06K 9/32* (2006.01)

(52) U.S. Cl.
USPC ............ 382/294; 345/620; 378/4; 382/115; 382/128; 382/131; 382/209; 382/224; 600/407; 600/410; 600/413; 600/420

(58) Field of Classification Search
CPC ... A61B 6/5235; G06T 11/008; G06T 7/0024
See application file for complete search history.

(56) References Cited

U.S. PATENT DOCUMENTS

| | | | |
|---|---|---|---|
| 6,718,055 B1 * | 4/2004 | Suri | 382/128 |
| 6,792,066 B1 * | 9/2004 | Harder et al. | 378/4 |
| 7,158,692 B2 * | 1/2007 | Chalana et al. | 382/294 |
| 7,590,440 B2 * | 9/2009 | Lau et al. | 600/413 |
| 7,751,605 B2 * | 7/2010 | G ndel et al. | 382/128 |
| 8,108,024 B2 * | 1/2012 | Carlsen et al. | 600/407 |
| 2003/0174872 A1 * | 9/2003 | Chalana et al. | 382/128 |
| 2003/0228042 A1 * | 12/2003 | Sinha | 382/131 |
| 2004/0264741 A1 * | 12/2004 | Omatsu et al. | 382/115 |
| 2006/0052690 A1 * | 3/2006 | Sirohey et al. | 600/420 |
| 2007/0127790 A1 * | 6/2007 | Lau et al. | 382/128 |
| 2007/0230761 A1 * | 10/2007 | Gundel et al. | 382/131 |
| 2008/0004519 A1 * | 1/2008 | Theriault | 600/410 |
| 2008/0009707 A1 * | 1/2008 | Theriault | 600/410 |
| 2008/0051648 A1 * | 2/2008 | Suri et al. | 600/407 |
| 2009/0080779 A1 * | 3/2009 | Chefd'hotel et al. | 382/209 |
| 2009/0190840 A1 * | 7/2009 | Gundel | 382/224 |
| 2010/0091035 A1 * | 4/2010 | Kirchberg et al. | 345/620 |

OTHER PUBLICATIONS

Kim KW, Lee JM, Klotz E, Park HS, Lee DH, Kim JY, Kim SJ, Kim SH, Lee JY, Han JK, Choi BI, "Quantitative CT Color Mapping of the Arterial Enhancement Fraction of the Liver to Detect Hepatocellular Carcinoma", Radiology, in press: Radiology: vol. 250: No. 2; Feb. 2009.

* cited by examiner

*Primary Examiner* — Tsung-Yin Tsai

(57) ABSTRACT

A method and system for data dependent multi phase image visualization, includes: acquiring a plurality of series of image data acquisitions; registering the plurality of series of image data acquisitions to a same reference series to create a plurality of registered series; combining information from the registered series to create a new series; creating a further new series by a selection decision based on combination rules from information from the plurality of registered series and the new series; and displaying the further new series.

11 Claims, 4 Drawing Sheets

METHOD AND SYSTEM FOR DATA DEPENDENT MULTI PHASE VISUALIZATION

CROSS-REFERENCE TO RELATED APPLICATION AND CLAIM OF PRIORITY

Specific reference is hereby made to U.S. Provisional Patent Application No. 61/087,766, filed Aug. 11, 2008 in the names of inventors Bernhard Geiger, Ernst Klotz, and Christophe Chefd'hotel, entitled DATA DEPENDENT MULTI PHASE VISUALIZATION—APPLICATION TO HEPATIC PERFUSION INDEX VISUALIZATION, and which is hereby incorporated herein by reference and whereof the benefit of priority is claimed.

FIELD OF THE INVENTION

The present invention relates generally to the field of imaging apparatus and more particularly to multi phase visualization, such as for medical imaging as may be utilized in hepatic perfusion visualization and for other imaging applications.

BACKGROUND OF THE INVENTION

Perfusion data is used to diagnose a wide range of pathologies in the human body by showing the flow of injected contrast agents. A perfusion study comprises several acquisitions, typically one before the injection and one or more acquisitions at time intervals after the injection. Studies show the spread of contrast agent in different tissue.

In order to detect subtle changes, the different time series resulting from the acquisitions have to be combined in an appropriate way so that the enhancement attributable to the contrast agent can be calculated locally and visualized. Typically, a form of registration, deformable or rigid, is used to compensate for patient motion. Then the data can be compared, subtracted, etc., and the flow information can be extracted. The result of the flow calculation is either displayed in separate views, or it is merged back into one of the series to provide the user with anatomical context. This merging is usually done for the complete image, using a blending.

As an example, the calculation of the Hepatic perfusion index is cited. In the example, three phases are acquired: a Native phase N, without contrast, an Arterial phase A, wherein contrast has entered the arterial system, and a Venous phase V, wherein contrast has filled the venous system. Then these different time series are deformed to compensate for patient motion, including the effects of breathing. After deformation, the time series are in the same coordinate system and can be compared voxel by voxel. The Hepatic perfusion index HPI is then calculated as $$HPI=(A-N)/\text{Max}(A-N, V-N).$$

This value is displayed in a color-coded scheme. It has been shown in publications that the HPI improves the detection of subtle changes in the liver related to HCC (liver tumors). See, for example, Kim K W, Lee J M, Klotz E, Park H S, Lee D H, Kim J Y, Kim S J, Kim S H, Lee J Y, Han J K, Choi Bl, "Quantitative CT Color Mapping of the Arterial Enhancement Fraction of the Liver to Detect Hepatocellular Carcinoma", Radiology, in press: Radiology: Volume 250: Number 2; February 2009. It is noted that co-author E. Klotz is a named inventor in the present application.

However the color coded image generally also shows enhancement outside the liver, where it is typically not of any value and, in fact, may tend to obscure anatomical information and/or landmarks and can distract the focus of attention of the viewer. Even inside the target organ, such as a liver, the arteries are enhanced as well, making it necessary to inspect carefully to distinguish lesions from arteries. See FIG. 2 for an example of an image without application of the present invention.

SUMMARY OF THE INVENTION

In accordance with principles of the present invention, local anatomical information is used to select locally relevant information from each of the series N, A, and V. Based on a series of thresholds, we decide which image to display. Using thresholds for tissue specific intensities and for enhancement values, we can reduce unnecessary HPI areas and bring together anatomical information.

In accordance with principles of the present invention, a method for data dependent multi phase image visualization comprises: acquiring a plurality of series of image data acquisitions; registering the plurality of series of image data acquisitions to a same reference series to create a plurality of registered series; combining information from the registered series to create a new series; and creating a further new series by a selection decision based on combination rules from information from the plurality of registered series and the new series.

In accordance with principles of the present invention, the method includes a step of rendering the further new series.

In accordance with principles of the present invention, the step of registering the plurality of series of image data acquisitions to a same reference series comprises registering to one of the series of data acquisitions.

In accordance with principles of the present invention, the step of creating a further new series by a selection decision based on combination rules comprises utilizing thresholds.

In accordance with principles of the present invention, the step of creating a further new series by a selection decision based on combination rules comprises utilizing thresholds using three series, wherein a first series N corresponds to a native phase image, a second series A corresponds to an arterial phase image, and a third series V corresponds to a venous phase image.

In accordance with principles of the present invention, the combination rules comprise the steps of:
if the native phase image value is below a first predetermined threshold, then using the native phase image, if the native phase image value is above a second predetermined threshold, then using the native phase image, if the arterial phase image value is above a third predetermined threshold, then using the arterial phase image; if a difference A−N is above a fourth predetermined threshold, then using the arterial phase image, if a difference V−N is above a fifth predetermined threshold, then using the venous phase image, if Max (A−N, V−N) is lower than a sixth predetermined threshold, then using the native phase image, and in all other cases, displaying the new series.

In accordance with principles of the present invention, the step of combining information from the registered series to create a new series comprises including in the combining: information from any of the plurality of registered series pertaining to any of: a measurement of perfusion, a Hepatic perfusion index HPI, diffusion, ventilation, flow, blood flow speed, change, fiber direction, or other enhancement.

In accordance with principles of the present invention the combination rules comprise: integrating back into an image specific information relating to any of: a measurement of perfusion, a Hepatic perfusion index HPI, diffusion, ventilation, flow, blood flow speed, change, fiber direction, or other enhancement.

In accordance with principles of the present invention, a system for data dependent multi phase image visualization, comprises:

a memory device for storing a program and other data; and
a processor in communication with the memory device, the processor being operative with the program to perform:
acquiring a plurality of series of image data acquisitions;
registering the plurality of series of image data acquisitions to a same reference series to create a plurality of registered series;
combining information from the registered series to create a new series; and
creating a further new series by a selection decision based on combination rules from information from the plurality of registered series and the new series.

In accordance with principles of the present invention, a computer program product comprises a computer useable medium having computer program logic recorded thereon for program code for performing data dependent multi phase image visualization by:

acquiring a plurality of series of image data acquisitions;
registering the plurality of series of image data acquisitions to a same reference series to create a plurality of registered series;
combining information from the registered series to create a new series; and
creating a further new series by a selection decision based on combination rules from information from the plurality of registered series and the new series.

BRIEF DESCRIPTION OF THE DRAWING

The invention will be more fully understood from the following detailed description, in conjunction with the drawings, in which.

DETAILED DESCRIPTION OF PREFERRED EMBODIMENTS OF THE INVENTION

For the purposes of the present description, figures in black and white are sufficient to illustrate the principles involved and are herein so utilized such that the differences being pointed out are readily apparent from the black and white image. In practice, color is readily and desirably utilized, affording a practitioner a clearer and more obvious indication of the differences being observed.

Figure 2:
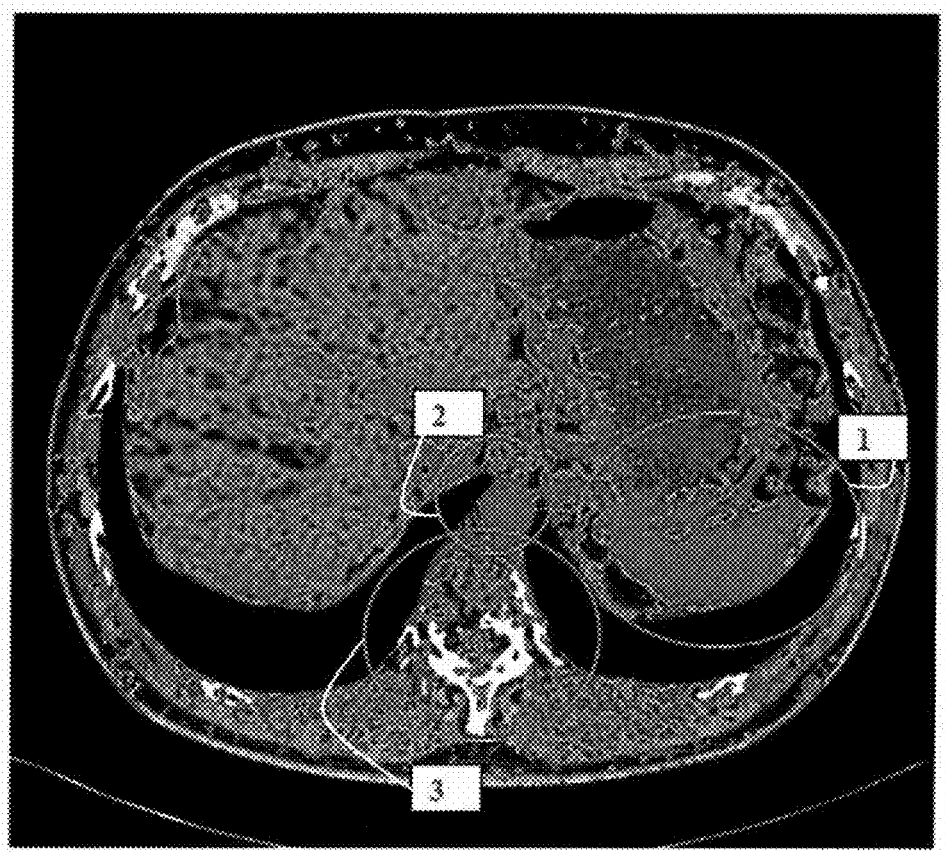
FIG. 2 shows a medical image such as may be obtained by known standard medical imaging devices, shown for the purpose of comparison, without application of the present invention.
Figure 3:
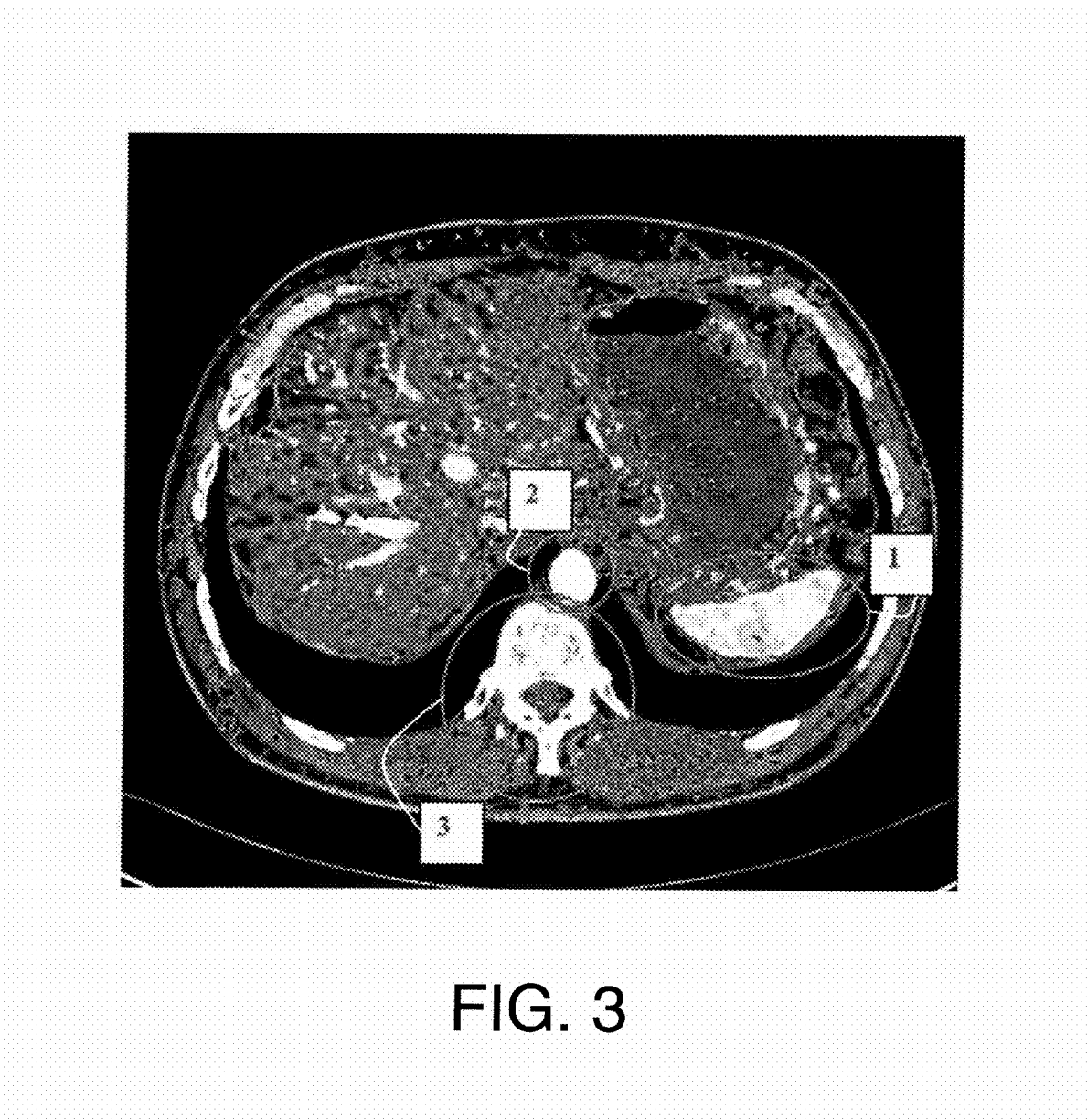
FIG. 3 shows a medical image with essentially the same subject matter as that of FIG. 2, but after processing in accordance with principles of the present invention.

FIG. 3 shows an example of the result of the method in accordance with the present invention. The image shown in FIG. 3 should be compared with that shown in FIG. 2 which is without application of principles of the present invention. FIG. 3 combines portions of N, A, and V and the HPI in one single dataset, showing more useful anatomical information than is the case otherwise. The arteries and veins are visible inside the liver. Outside the liver, bone and spleen are visible.

Figure 1:
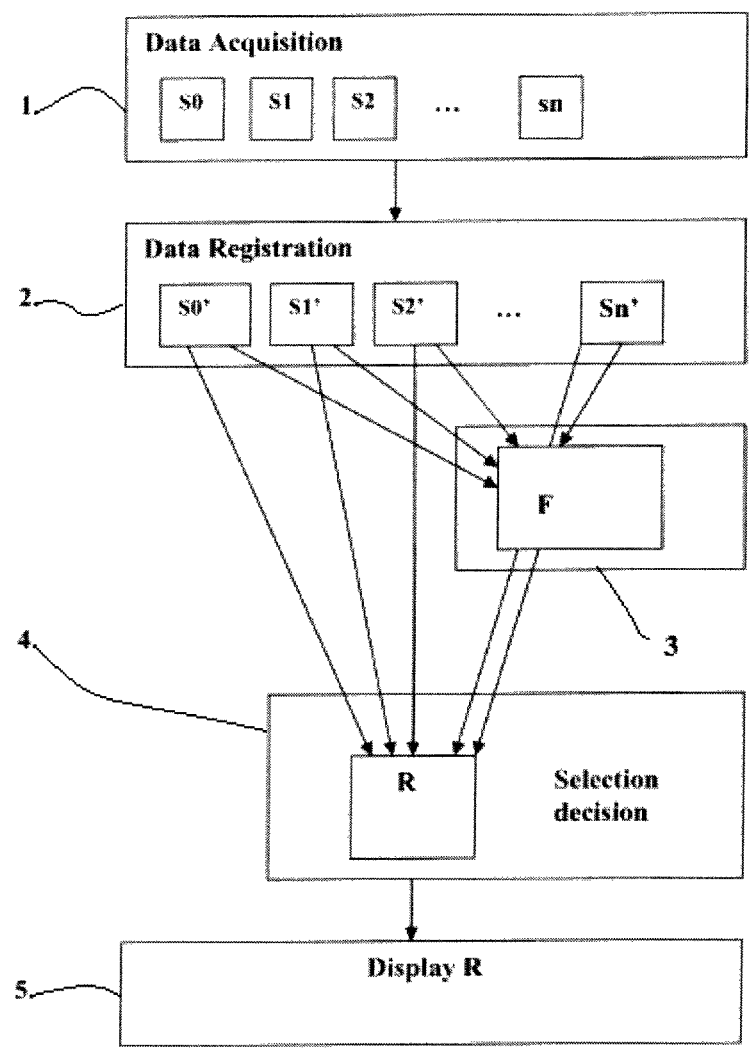
FIG. 1 shows a symbolic diagram of various steps in accordance with principles of the present invention.

FIG. 1 shows steps in accordance with the present invention in the form of a flow diagram.

Step 1 shows the data acquisition of several series of acquisitions, S0, S1, S2 . . . Sn, utilizing, for example, CT, MR, Ultrasound, and X-ray. The data may be in the form of two-dimensional (2D) images and/or volumetric data sets.

In Step 2, all series are registered to the same reference series using known registration methods, including deformable and rigid registration methods, resulting in a registered series S0', S1', S2' . . . Sn'. The reference frame can be any of the series.

In step 3, a new series (F) is created, combining information from all series. This can be a measurement of perfusion, diffusion, ventilation, flow, change, and so forth. For example, as was previously mentioned, the hepatic perfusion index HPI can be calculated as $$HPI=(A-N)/\text{Max}(A-N, V-N)$$

wherein, as before, the symbols represent the three phases acquired: a Native phase N (without contrast), an Arterial phase A (wherein contrast has entered the arterial system) and a Venous phase V (wherein contrast has filled the venous system).

In step 4 a further new series (R) is created by selection decision in accordance with principles of the present invention, based on a set of combination rules that combine the new information from the series (F) created in step 3, and the registered series S0', S1', S2' . . . Sn' resulting from step 2.

This new series (R) is rendered on a screen in step 5.

An exemplary set of rules currently used in step 4 of the present exemplary embodiment of the present invention for arriving at the selection decision are thresholds, using three series N, A, V is shown in Table 1, as follows:

TABLE 1

| NAME | DEFAULT VALUE | FUNCTION |
|---|---|---|
| CTLIVER | −200 [HU] | If the native image value is below this threshold, use the native image. |
| CTBONE | 100 [HU] | If the native image value is above this threshold, use the native image |
| CTARTERIAL | 200 [HU] | If the arterial image value is above this threshold, use the arterial image |
| CTVENOUS | 200 [HU] | If the venous image value is above this threshold, use the venous image |
| CTARTERIALDELTA | 80 | If the difference A-N is above this threshold, use the arterial image |
| CTVENOUSDELTA | 60 | If the difference V-N is above this threshold, use the venous image |
| CTNOISE | 12 | If Max(A-N, V-N) is lower than this threshold, use the native image. |

In all other cases display F.

However, each of the different datasets provides different information. In the native data, for example, we see calcifications but no blood vessels. In the arterial phase we see blood vessels. In the later phase we see liver tissue, etc. We can apply a set of rules to choose which information from which dataset to use for the final display (R).

As was stated above, specific information, for example, HPI, blood flow, speed, fiber direction, or other enhancement is not shown in an isolated image, that is, for example, an all black image except where blood flow occurs, but is integrated back into an image. This is usually done by using one of the original images and adding or blending the information (F) to it.

In accordance with principles of the present invention, a plurality of fewer than all images, or of all images, is utilized and a selection decision, or a set of rules, is applied to decide where to show which information.

Two principal reasons for this are that:

(a) the information (F) is not only calculated inside the lesion/organ, etc., where it makes sense. For example, the HPI is not only calculated inside a tumor, but also inside bone, kidneys, etc. The set of rules are used to suppress display in areas that are not meaningful, and help therefore to focus attention on the important areas; and (b) the areas outside of meaningful information (F) are needed to provide anatomical context, such that, for example, one can see that one is at the level of the left kidney, and so forth.

However, each of the different datasets provides different information. For example, in the native data, calcifications may typically be seen, but not blood vessels. In the arterial phase blood vessels are typically seen. In the later phase, typically liver tissue, etc. may be seen. The set of rules in accordance with the invention is applied to choose which information from which dataset is to be used for the final display (R)

Reference is made to the exemplary set of rules in Table 1 for the following more detailed explanation of the set of rules, the HPI, and an understanding of the reason or reasons for each rule. The rules are referred to in order from the top of Table 1 to the bottom, using the rule names.

Rule (1), CTLIVER states that this area is NOT liver: use the native image in this area;

Rule (2), CTBONE states that this area is NOT liver: use the native image in this area;

Rule (3), CTARTERIAL states that this area includes arteries: use the arterial image to show arteries;

Rule (4), CTVENOUS states that this area most likely is a vein: show the venous image in this area Rule (5), CTARTERIALDELTA states that this area shows strong arterial enhancement: show arterial image in this area;

Rule (6), CTVENOUSDELTA states that this area shows strong late enhancement: show venous image in this area; and Rule (7), CTNOISE states that result (F) is below a noise threshold: show native image.

All areas that pass the foregoing tests will display (F).

This implies that (a) (F) will not be displayed in arteries (Rule (5)) or veins (Rule (6)) or on top of bones (Rule (2)), and so forth, corresponding to a selective display of (F); and (b) the final image comprises data from all images (N, A, V, F), corresponding to more information in the display than heretofore.

These rules have been derived based on reasoning on known Hounsfield values for different anatomical objects and based on knowledge about perfusion, for example, that arteries enhance statistically by certain known amounts. Reference is made to Hounsfield units which are calculated to correspond to the attenuation of x-rays measured within a particular sample of tissue. The pixel value in a CT image, for example, is generally reported in Hounsfield units.

Other means and criteria can also be used for deriving a set of similar rules. For example, image features, such as tissue classes, Hounsfield unit (HU) ranges, enhancement values such as differences between datasets, and so forth, can be described as multi dimensional feature vectors. Each voxel in each dataset i can be associated with a vector Vi of dimension d. A feature in this vector could be, for example "HU values less than 200" or, for another example, "difference of HU(i)−HU(0)>100".

Rules are then defined as logical combinations of vectors to decide which voxel is displayed. These rules, and the feature vectors themselves can be calculated automatically using supervised learning methods wherein, typically, a user annotates images. Furthermore, unsupervised learning can be used, such as for example, clustering of feature space, or a combination of empirical/automated methods.

Referring again to FIGS. 2 and 3 for a more detailed explanation of the application of the present invention, it is noted that three areas are marked by generally circular or elliptical boundaries labeled correspondingly in FIGS. 2 and 3 as areas 1, 2, and 3. As was stated above, FIG. 3 shows an image with the application of principles in accordance with the present invention and FIG. 2 shows the image without such application, for the purpose of comparison in the explanation.

In FIG. 2, the spleen, in area 1, has been colored uniformly because the mapping (F) applies to it, or in the case of a black and white image, it has been marked in a given shade. In FIG. 3, after using the set of rules in accordance with principles of the invention, the spleen, in area 1, is now rendered from the late acquisition, displaying the normal appearance shape of a spleen which gives the radiologist a context for viewing the image or it can even show pathology if such is present.

By using only (F), this useful information would have been lost, (F) being only useful for the liver. The rule for area 1 in FIG. 3 in accordance with the invention, was rule 6.

In FIG. 2, the aorta, in area 2, is rendered in uniform color using only (F). In FIG. 3, in accordance with the principles of the invention, the aorta, in area 2, is rendered using the information from the arterial phase, resulting in bright contrast enhancement, brighter in the present black and white rendition than the corresponding image portion in FIG. 2. Furthermore, useful information like the presence of calcifications might be visible. Rule 3 and Rule 5 from the foregoing table are applied to this area.

In FIG. 2, without the benefit of the present invention, the spine, in area 3, appears somewhat fuzzy on its upper left side of the cross-section. In FIG. 3 the spine, in area 3, is partially rendered (in color where color is being used, and herein in black and white) in a lighter shade from applying (F) in accordance with principles of the present invention. By the benefit of Rule 2 from the foregoing table, a clean image of a vertebra of diagnostic quality is displayed which looks more like a complete verterbra than the corresponding area display in FIG. 2.

Figure 4:
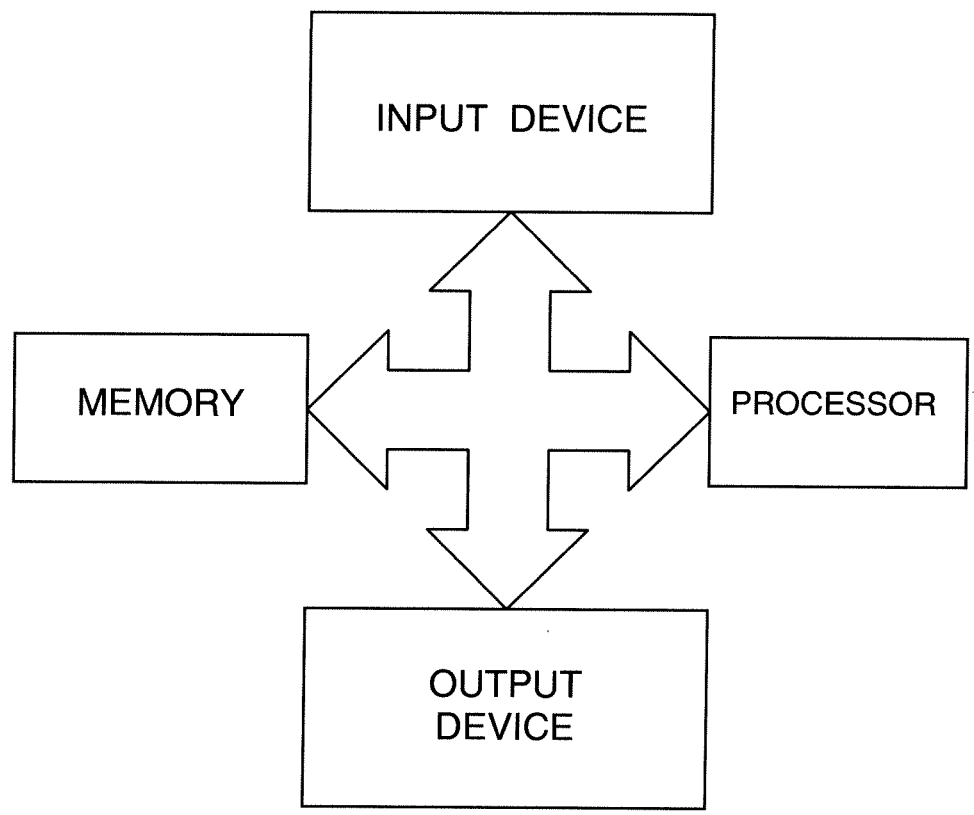
FIG. 4 shows in block schematic form a computer such as may be utilized for implementation of an embodiment of the present invention.

As will be apparent, the present invention for a method and system for data dependent multi phase visualization is intended to be implemented with the use and/or application of imaging equipment in conjunction with a programmed digital computer. FIG. 4 shows in general terms and in basic schematic form a digital processor coupled for two way data communication with an input device, an output device, and a memory device for storing a program and other data. The input device is so designated in broad terms as a device for exchanging data, for example, relating to an image or images, or interactive commands for processing in accordance with the present invention. For example, an input may be from an imaging device, such as a device incorporated in a CATSCAN, X-ray machine, an MRI or other device, or a stored image, or by communication with another computer or device by way of direct connection, a modulated infrared beam, radio, land line, facsimile, or satellite as, for example, by way of the World Wide Web or Internet, or any other appropriate source of such data. The output device may be for data, commands, and/or it may include a computer type display device using any suitable apparatus such as a cathode-ray kinescope tube, a plasma display, liquid crystal display, and so forth, and serve as a user interface as utilized in the described exemplary embodiments, or it may or may not include a device for rendering an image and may include a memory for storing an image, or measurement parameters or commands for further processing, or for viewing, or evaluation, as may be convenient, or it may utilize a connection or coupling including such as are noted above in relation to the input device. The processor is operative with a program set up in accordance with the present invention for implementing steps of the invention. Such a programmed computer may interface readily through communications media such as land line, radio, the Internet, and so forth for image data acquisition and transmission.

The invention may be readily implemented, at least in part, in a software memory device and packaged in that form as a software product. This can be in the form of a computer program product comprising a computer useable medium having computer program logic recorded thereon for program code for performing the method of the present invention.

The present invention has also been explained in part by way of examples using illustrative exemplary embodiments. It will be understood that the description by way of exemplary embodiments is not intended to be limiting and that, while the present invention is broadly applicable, it is helpful to also illustrate its principles, without loss of generality, by way of exemplary embodiments relating to an important field of application for the present invention, namely, to computer vision and imaging.

Moreover, it will also be understood that various changes and substitutions not necessarily explicitly described herein may be made without departing from the spirit and scope of the invention which is defined by the claims following.

What is claimed is:

1. A method for data dependent multi phase image visualization, comprising:
   acquiring a plurality of series of image data;
   registering said acquired plurality of series of image data to a same reference series of image data to create a plurality of registered series of image data, said plurality of registered series of image data comprising three series of image data of an anatomical region during phases of contrast medium distribution, said three series having a first series N that corresponds to a native phase image, a second series A that corresponds to an arterial phase image, and a third series V that corresponds to a venous phase image;
   combining information from said plurality of registered series of image data to create a new series of image data; and
   creating a further new series of image data by combining information from said plurality of registered series of image data and said new series of image data based on combination rules that utilize image feature measurements to select respective information from said plurality of registered series of image data and said new series of image data for the further new series of image data, said combination rules comprising the steps of:
     if a native phase image feature value is below a first predetermined threshold, then using said native phase image,
     if a native phase image feature value is above a second predetermined threshold, then using said native phase image,
     if an arterial phase image feature value is above a third predetermined threshold, then using said arterial phase image;
     if a difference A–N feature value is above a fourth predetermined threshold, then using said arterial phase image,
     if a difference V–N feature value is above a fifth predetermined threshold, then using said venous phase image,
     if Max (A–N, V–N) feature value is lower than a sixth predetermined threshold, then using said native phase image, and
     in all other cases, using said new series of image data.

2. A method as recited in claim 1, further comprising a step of rendering said further new series of image data.

3. A method as recited in claim 1, wherein:
   said step of registering said acquired plurality of series of image data to a same reference series of image data comprises registering said acquired plurality of series of image data to one of said acquired plurality of series of image data.

4. A method as recited in claim 1, wherein
   said step of combining information from said plurality of registered series of image data to create a new series of image data comprises combining information from any of said plurality of registered series of image data pertaining to any of: a measurement of perfusion, a Hepatic perfusion index HPI, diffusion, ventilation, flow, blood flow speed, change, fiber direction, or other enhancement.

5. A method as recited in claim 1, wherein said combination rules further comprise:
   integrating back into an image from any of said plurality of registered series of image data specific information relating to any of: a measurement of perfusion, a Hepatic perfusion index HPI, diffusion, ventilation, flow, blood flow speed, change, fiber direction, or other enhancement.

6. A system for data dependent multi phase image visualization, comprising:
   a memory device for storing a program and other data; and
   a processor in communication with said memory device, said processor operative with said program to perform:
     acquiring a plurality of series of image data;
     registering said acquired plurality of series of image data to a same reference series of image data to create a plurality of registered series of image data, said plurality of registered series of image data comprising three series of image data of an anatomical region during phases of contrast medium distribution, said three series having a first series N that corresponds to a native phase image, a second series A that corresponds to an arterial phase image, and a third series V that corresponds to a venous phase image ;
     combining information from said plurality of registered series of image data to create a new series of image data; and
     creating a further new series of image data by combining information from said plurality of registered series of image data and said new series of image data based on combination rules that utilize image feature measurements to select respective information from said plurality of registered series of image data and said new series of image data for the further new series of image data, said combination rules, comprising the steps of:
- if a native phase image feature value is below a first predetermined threshold, then using said native phase image,
- if a native phase image feature value is above a second predetermined threshold, then using said native phase image,
- if an arterial phase image feature value is above a third predetermined threshold, then using said arterial phase image;
- if a difference A–N feature value is above a fourth predetermined threshold, then using said arterial phase image,
- if a difference V–N feature value is above a fifth predetermined threshold, then using said venous phase image,
- if Max (A–N, V–N) feature value is lower than a sixth predetermined threshold, then using said native phase image, and
- in all other cases, using said new series of image data.

7. A system as recited in claim 6 for data dependent multi phase image visualization, wherein said processor is operative to further perform:
rendering said further new series of image data.

8. A system as recited in clam 6 for data dependent multi phase image visualization, wherein said registering said acquired plurality of series of image data to a same reference series of image data comprises registering said acquired plurality of series of image data to one of said acquired plurality of series of image data.

9. A system as recited in claim 6 for data dependent multi phase image visualization, wherein said combining information from said plurality of registered series of image data to create a new series of image data comprises
combining information from any of said plurality of registered series of image data pertaining to any of: a measurement of perfusion, a Hepatic perfusion index HPI, diffusion, ventilation, flow, blood flow speed, change, fiber direction, or other enhancement.

10. A system as recited in claim 6 for data dependent multi phase image visualization, wherein said creating a further new series of image data comprises
integrating back into an image from any of said plurality of registered series of image data specific information relating to any of: a measurement of perfusion, a Hepatic perfusion index HPI, diffusion, ventilation, flow, blood flow speed, change, fiber direction, or other enhancement.

11. A non-transistory computer readable medium comprising computer program logic recorded thereon for program code for performing data dependent multi phase image visualization by:
acquiring a plurality of series of image data;
registering said acquired plurality of series of image data to a same reference series of image data to create a plurality of registered series of image data, said plurality of registered series of image data comprising three series of image data of an anatomical region during phases of contrast medium distribution, said three series having a first series N that corresponds to a native phase image, a second series A that corresponds to an arterial phase image, and a third series V that corresponds to a venous phase image;
combining information from said plurality of registered series of image data to create a new series of image data; and
creating a further new series of image data by combining information from said plurality of registered series of image data and said new series of image data based on combination rules that utilize image feature measurements to select respective information from said plurality of registered series of image data and said new series of image data for the further new series of image data, said combination rules comprising the steps of:
- if a native phase image feature value is below a first predetermined threshold, then using said native phase image,
- if a native phase image feature value is above a second predetermined threshold, then using said native phase image,
- if an arterial phase image feature value is above a third predetermined threshold, then using said arterial phase image;
- if a difference A–N feature value is above a fourth predetermined threshold, then using said arterial phase image,
- if a difference V–N feature value is above a fifth predetermined threshold, use said venous phase image,
- if Max (A–N, V–N) feature value is lower than a sixth predetermined threshold, use said native phase image, and
- in all other cases, using said new series of image data.

* * * * *